(12) United States Patent
Erasala et al.

(10) Patent No.: US 9,788,741 B2
(45) Date of Patent: *Oct. 17, 2017

(54) METHOD AND SYSTEM FOR EVALUATION OF FUNCTIONAL CARDIAC ELECTROPHYSIOLOGY

(71) Applicant: Genetesis LLC, Cincinnati, OH (US)

(72) Inventors: Vineet Erasala, Mason, OH (US); Peeyush Shrivastava, Mason, OH (US); Emmanuel T. Setegn, Cincinnati, OH (US)

(73) Assignee: GENETESIS LLC, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/220,982

(22) Filed: Jul. 27, 2016

(65) Prior Publication Data
US 2016/0367161 A1     Dec. 22, 2016

Related U.S. Application Data

(63) Continuation of application No. 14/941,455, filed on Nov. 13, 2015, now Pat. No. 9,433,363.
(Continued)

(51) Int. Cl.
*A61B 5/04*         (2006.01)
*A61B 5/00*         (2006.01)
(Continued)

(52) U.S. Cl.
CPC ........ *A61B 5/04007* (2013.01); *A61B 5/0035* (2013.01); *A61B 5/0044* (2013.01); *A61B 5/021* (2013.01); *A61B 5/024* (2013.01); *A61B 5/04008* (2013.01); *A61B 5/04011* (2013.01); *A61B 5/055* (2013.01); *A61B 5/4064* (2013.01);
(Continued)

(58) Field of Classification Search
None
See application file for complete search history.

(56) References Cited

U.S. PATENT DOCUMENTS

| | | | |
|---|---|---|---|
| 8,553,956 B2 | 10/2013 | Wu et al. | |
| 2002/0103428 A1* | 8/2002 | deCharms | A61B 5/055 600/410 |

(Continued)

OTHER PUBLICATIONS

Jurkko R, Mantynen V, Tapanainen JM, Montonen J, Vaananen H, Parikka H, Toivonen L. Non-invasive detection of conduction pathways to left atrium using magnetocardiography: validation by intra-cardiac electroanatomic mapping. Europace. Feb. 2009;11(2):169-77.*

(Continued)

*Primary Examiner* — Ankit D Tejani
(74) *Attorney, Agent, or Firm* — Wilson Sonsini Goodrich & Rosati

(57) ABSTRACT

An organ evaluation device, system, or method is configured to receive electrophysiological data from a patient or model organism and integrates the data in a computational backend environment with anatomical data input from an external source, spanning a plurality of file formats, where the input parameters are combined to visualize and output current density and/or current flow activity having ampere-based units displayed in the spatial context of heart or other organ anatomy.

20 Claims, 11 Drawing Sheets

Related U.S. Application Data

(60) Provisional application No. 62/181,599, filed on Jun. 18, 2015, provisional application No. 62/181,567, filed on Jun. 18, 2015.

(51) Int. Cl.
| | |
|---|---|
| *A61B 5/021* | (2006.01) |
| *A61B 5/024* | (2006.01) |
| *A61B 5/055* | (2006.01) |
| *A61B 6/03* | (2006.01) |
| *A61B 6/00* | (2006.01) |
| *A61B 8/08* | (2006.01) |
| *A61B 90/00* | (2016.01) |
| *A61B 5/0205* | (2006.01) |
| *A61B 5/01* | (2006.01) |

(52) U.S. Cl.
CPC .......... *A61B 5/7235* (2013.01); *A61B 5/7278* (2013.01); *A61B 5/7282* (2013.01); *A61B 5/743* (2013.01); *A61B 5/7475* (2013.01); *A61B 6/032* (2013.01); *A61B 6/485* (2013.01); *A61B 8/08* (2013.01); *A61B 5/01* (2013.01); *A61B 5/02055* (2013.01); *A61B 2090/374* (2016.02); *A61B 2090/378* (2016.02); *A61B 2090/3762* (2016.02); *A61B 2562/0223* (2013.01); *A61B 2576/023* (2013.01); *A61B 2576/026* (2013.01)

(56) References Cited

U.S. PATENT DOCUMENTS

| | | | |
|---|---|---|---|
| 2003/0018277 A1 | 1/2003 | He | |
| 2011/0160546 A1 | 6/2011 | Madsen | |
| 2012/0284332 A1* | 11/2012 | Pradeep | G06Q 30/0269 709/204 |
| 2012/0310107 A1 | 12/2012 | Doidge et al. | |
| 2013/0057385 A1 | 3/2013 | Murakami et al. | |
| 2013/0324832 A1* | 12/2013 | Wu | A61B 5/04005 600/409 |
| 2015/0080703 A1* | 3/2015 | Reiman | A61B 5/4848 600/409 |

OTHER PUBLICATIONS

International Application No. PCT/US2016/038209 International Search Report and Written Opinion Mailed Sep. 14, 2016.
U.S. Appl. No. 14/941,455 First Action Interview Pre-Interview Communication Mailed Feb. 17, 2016.

* cited by examiner

METHOD AND SYSTEM FOR EVALUATION OF FUNCTIONAL CARDIAC ELECTROPHYSIOLOGY

CROSS-REFERENCE

This application is a continuation of U.S. application Ser. No. 14/941,455, filed Nov. 13, 2015, which claims the benefit of U.S. Provisional Application No. 62/181,567, filed Jun. 18, 2015, and U.S. Provisional Application No. 62/181,599, filed Jun. 18, 2015, each of which are incorporated herein by reference in their entireties.

SUMMARY

Described herein are devices, systems, media, and methods for non-invasively evaluating an organ. Described herein are devices, systems, media, and methods for non-invasively evaluating the function of an organ of an individual. Described herein are devices, systems, media, and methods for non-invasively diagnosing and localizing structural abnormalities in an organ of an individual. In some embodiments, the organ being monitored is a brain. In some embodiments, the organ being monitored is a heart. In some embodiments, the organ being monitored is a digestive organ including the liver, gallbladder, pancreas, stomach, small bowel, and large bowel.

Described herein are devices, systems, media, and methods for accurately non-invasively diagnosing and localizing cardiac arrhythmia. Accurate evaluation of cardiac arrhythmia with localization of an arrhythmia facilitates accurate and successful arrhythmia treatment while further benefiting the individual and the physician by enabling reduced radiation exposure during the procedure. The use of creating distributed current vectors in units of amperes based upon magnetic field measurements of electrical activity allows access to deeper sources of electrical activity in the heart through providing a physiological basis for rhythm or lack thereof, as well as representing spatially the electrical activity of heart tissue with anatomical context. These measurements allow access to tangential fields and insight into the endocardium, vital areas of interest for clinicians skilled in this art. These measurements create vector representations of the organ anatomy and provide graphical, three dimensional representations showing the anatomy and electrophysiology including abnormalities thereof, throughout the depth of the organ.

Described herein is a system for evaluating an organ of an individual in need thereof, comprising: an organ electromagnetic sensor configured to sense a magnetic field associated with said organ, and to couple with a computing device, wherein said computing device is configured to: receive a magnetic field data associated with said organ from said electromagnetic sensor; translate said magnetic field data associated with said organ to at least one electrical current vector associated with said organ; and combine graphically said at least one electrical current vector with an image of said organ to generate an electrical current density map of said organ for use in evaluating said organ. In some embodiments, said evaluation of said organ is non-invasive. In some embodiments, said computing device is further configured to display said electrical current density map together with said at least one electrical current vector. In some embodiments, said organ is a heart. In some embodiments, said computing program is further configured to identify an arrhythmia. In some embodiments, said computing program is further configured to identify an arrhythmogenic focus in said heart. In some embodiments, said current map comprises one or more colored areas each corresponding to said current density associated with each of said colored areas. In some embodiments, said organ is a brain. In some embodiments, said computing program is further configured to identify an ischemic focus in said brain. In some embodiments, said processor receives said image of said organ from an imaging system. In some embodiments, said imaging system comprises an ultrasound. In some embodiments, said imaging system comprises a fluoroscope. In some embodiments, said image is a three dimensional image. In some embodiments, said three dimensional image is generated from two or more two dimensional images. In some embodiments, said program is configured to cause said processor to further receive demographic data associated with said individual. In some embodiments, said demographic data comprises one or more of age, race, gender, and medical history of said individual. In some embodiments, said received demographic data associated with said individual is used to identify a three dimensional image of an organ of a different individual, wherein the demographic data associated with said individual and demographic data associated with said different individual are essentially identical in one or more of said age, said race, said gender, and said medical history. In some embodiments, said image comprises said image of said organ of said different individual. In some embodiments, said program is configured to cause said processor to further receive biometric data associated with said individual. In some embodiments, said biometric data comprises one or more of heart rate, blood pressure, and temperature of said individual. In some embodiments, said computing program is further configured to generate an evaluation of said organ comprising said electrical current vector map and said biometric data.

Described herein is a computer implemented method for evaluation through detecting, localizing and quantifying arrhythmogenic substrates in the heart, comprising the steps of providing an electromagnetic sensor device having at least one processor configured to execute instructions from a software application; and providing a computer backend having at least one processor configured to execute instructions from a software application having a plurality of inputs and outputs; and providing electrical activity data as function of electromagnetic activity in magnetic data values for cardiac tissue as an output of said sensor and input of said backend, wherein said data includes a representative series of recordings defining distributed cardiac electromagnetic activity in three dimensional vector space during a specified time period and specified time period markers for the aforementioned recordings; and utilizing anatomical data for cardiac tissue, wherein said data includes a plurality of data files providing electronic three dimensional mappings of heart geometry embodied on non-volatile memory; and processing by said computer processor the input magnetic activity data provided by said sensor and input anatomical data, wherein the step of processing includes calculating a plurality of distributed, spatially accurate electrical current vectors (with units of amperes) in three dimensional space and uniquely identifying and outputting them in reference to anatomical structures found within said heart geometry files; and displaying both electrical current vectors and anatomical data simultaneously through the process of image registration, wherein said registration involves functional overlay of three dimensional anatomical reconstruction with electroanatomical data provided by computational processing. In some embodiments, the method additionally comprises the steps of: providing a software application by means of which a user interface through which computer processing may occur is created; and providing a system for the importation and utilization of two dimensional or three dimensional data embodied in a plurality of filetypes relating to anatomical geometry; and providing a system for the importation and utilization of magnetic field data provided by a said electromagnetic sensor device. In some embodiments, the method additionally comprises the steps of: providing an electronic visual display software application by means of which both magnetic amplitude waveforms and which distribution vectors can be observed; and interpreting by said application components of three dimensional anatomical distributed current models through a spatially oriented user interface; and said user interface allows for manual manipulation through said user interface of spatial observation for the individual; and wherein said manipulation includes alteration of said image through said computational backend and alteration includes manipulation of nonstructural qualitative factors including but not limited to as color, position, and opacity. In some embodiments, said accumulated electrical vector data involve identification of unique spatial landmarks and structures; and said embodied, predetermined anatomical image data involve unique identification of corresponding structures and landmarks; and said integration of electrical vector and electronically imported anatomical image data allows for joint registration of electrical and anatomical data based on landmark and structure identification, wherein registration refers to data-skin overlay of a three dimensional image such that quantitative data is displayed qualitatively with a plurality of color gradients bound to certain quantitative scales in three dimensional space, with particular relation to said structures and landmarks. In some embodiments, said predetermined embodied anatomical data for selection comprises a plurality of indicated demographic and lifestyle factors, and wherein the demographics may involve but are not limited to factors of health status, age, gender, a priori illness, diet, smoking, and substance use. In some embodiments, the process of selection of said data involves external selection as a function of said factors. In some embodiments, the step of interpreting integrated vector-spatial data involves computational output through an individual. In some embodiments, the method additionally comprises the step of configuring electrical activity data provided by said processor, wherein the step of configuring includes determining the file format of the data provided. In some embodiments, the step of processing includes calculating distributed cardiac current vector activity in dynamic, real time parameters. In some embodiments, the method additionally comprises the steps of providing an activity database of said current density output having baseline activity recordings; and interpreting by said processor input magnetic data and externally selected anatomical data, wherein the step of interpreting includes comparing provided data with database baseline activity recordings; and evaluating by said processor the comparison of activity as a function of risk assessment, where greater deviations from accepted baseline activity are indicated as higher risk factors and are directly related. In some embodiments, said sensor is a Magnetocardiogram system with a network comprised of a plurality of said electromagnetic sensors.

Described herein is a computational method for detecting, localizing and quantifying arrhythmogenic substrates in the heart, comprising the steps of: providing an electromagnetic sensor device having at least one processor configured to execute instructions from a software application; and providing a computer backend having at least one processor configured to execute instructions from a software application having a plurality of inputs and outputs; and providing electrical activity data as function of electromagnetic activity in magnetic data values for cardiac tissue as an output of said sensor and input of said backend, wherein said data includes a representative series of recordings defining distributed cardiac electromagnetic activity in three dimensional vector space during a specified time period and specified time period markers for the aforementioned recordings; and utilizing anatomical data for cardiac tissue, wherein said data includes three dimensional mapping of heart geometry acquired by means of either reconstruction from a series of two dimensional images, or importing of a three dimensional file; and processing by said computer processor the input magnetic activity data provided by said sensor and input anatomical data, wherein the step of processing includes calculating a plurality of distributed, spatially accurate electrical current vectors (with units of amperes) in three dimensional space and uniquely identifying and outputting them in reference to anatomical structures; and displaying both electrical current vectors and anatomical data simultaneously through the process of image registration, wherein said registration involves functional overlay of three dimensional anatomical reconstruction with electroanatomical data provided by computational processing. In some embodiments, the method additionally comprises the steps of: providing a software application by means of which a user interface through which computer processing may occur is created; and providing a system for the importation and utilization of two or three dimensional data embodied in a plurality of filetypes relating to anatomical geometry; and providing a system for the importation and utilization of magnetic field data provided by a said electromagnetic sensor device. In some embodiments, the method additionally comprises the steps of: providing an electronic visual display by said software application by means of which both magnetic amplitude waveforms and which distribution vectors can be observed; and interpreting by said application components of three dimensional anatomical distributed current models through a spatially oriented user; and said user interface allows for manual manipulation through said user interface of spatial observation for the individual; and wherein said manipulation includes alteration of said image through said computational backend and alteration includes manipulation of nonstructural qualitative factors including but not limited to as color, position, and opacity. In some embodiments, said accumulated electrical vector data involve identification of unique spatial landmarks and structures; and said anatomical image data involve unique identification of corresponding structures and landmarks; and the integration of electrical vector and electronically imported anatomical image data allows for joint registration of electrical and anatomical data based on landmark and structure identification, wherein registration refers to data-skin overlay of a three dimensional image such that quantitative data is displayed qualitatively with a plurality of color gradients bound to certain quantitative scales in three dimensional space, with particular relation to said structures and landmarks. In some embodiments, the step of interpreting integrated vector-spatial data involves computational processes through an individual; and wherein said computational processes involve utilization of Maxwell's equations to solve for distributed cardiac current vectors for an individual. In some embodiments, the method additionally comprises the step of configuring electrical activity data provided by said processor, wherein the step of configuring includes determining the file format of the data provided. In some embodiments, the step of processing includes calculating distributed cardiac current vector activity in terms of ampere-based dynamic, real time parameters wherein the step of processing said cardiac current vectors involves the solution of an inverse problem using Maxwell's electromagnetic equations to determine the relationship between Magnetic Field and Current Density for an individual. In some embodiments, said sensor is a Magnetocardiogram system with a network comprised of a plurality of said electromagnetic sensors.

Described herein is a system for detecting, localizing and quantifying arrhythmogenic substrates in the heart for an individual, comprising: an electromagnetic sensor network and computer backend having at least one processor and memory, wherein said processor is configured to execute instructions from a software application to cause the electronic device to perform the following step; processing electrical activity data for cardiac tissue, wherein said data includes a representative series of recordings defining distributed cardiac electrical activity in three dimensional vector space during a specified time period and specified time period markers for the aforementioned recordings; and wherein the step of processing includes calculating a plurality of distributed, spatially accurate vectors with units of electrical current in three dimensional space and uniquely identifying them in reference to anatomical structures. In some embodiments, said accumulated electrical vector data involves identification of unique spatial landmarks and structures; and said anatomical image data involve unique identification of corresponding structures and landmarks; and said integration of electrical vector and anatomical image data allows for joint registration of electrical and anatomical data based on landmark and structure identification In some embodiments, the step of interpreting integrated vector-spatial data involves computational output through an individual. In some embodiments, the step of processing includes calculating distributed cardiac current vector activity as a function with outputs in units of amperes in dynamic real time.

DETAILED DESCRIPTION

Various organs of the mammalian body including, for example, the heart, brain, and digestive organs, may malfunction leading to disease. Accurate diagnoses of organ malfunction are critical in terms of being able to provide accurate therapy and avoid unintended complications.

For example, the heart coordinates contraction through an electrical current that travels through the myocardium of different regions of the heart in a predictable pattern in the healthy individual. If the travel of the electrical current through the heart is abnormal, an individual will typically suffer an aberrant cardiac contraction which may be diagnosed as an arrhythmia. Millions of patients suffer from cardiac arrhythmias, many of which are life threatening.

Arrhythmia is typically diagnosed based on both patient history and cardiac evaluation technology. Traditional cardiac evaluating modalities used to diagnose arrhythmia may include the electrocardiogram and Cardiac MRI.

Patients with certain arrhythmias diagnosed with the typical diagnostic approaches, which are based on patient history and the traditional evaluating modalities, are treated with cardiac catheter ablation. Studies show that the accuracy of cardiac catheter ablation based on the typical diagnostic approaches is only around 50-80%.

I. Organ Evaluation Devices and their Use

Disclosed herein are devices, systems, media, and methods configured to evaluate an organ of an individual in terms of, for example, the physiology of the organ or, for example, the anatomical structure of an organ. In some embodiments, an abnormality in an organ is identified using the devices, systems, media, and methods described herein. In some embodiments, an identified abnormality may be localized to a particular area of an organ.

The devices, systems, media or methods disclosed herein may be configured to evaluate the function of the brain of an individual who suffered an ischemic event. An ischemic event affecting the brain may, for example, cause a decrease or absence of an electrical current. Using the devices, systems, media, and methods described herein an area of decreased or absent electrical current in the brain is localized.

The devices, systems, media or methods disclosed herein may also be configured to evaluate an abnormality in the function of the heart of an individual with an irregular heartbeat. An irregular heartbeat may, for example, comprise an abnormal current flow pattern through the myocardium of the heart of the individual suffering from the arrhythmia. When used to evaluate the heart, the devices systems, media, and methods described herein may be configured to localize an abnormal current flow density or pattern in the myocardium of an individual and are thus configured to localize an arrhythmogenic focus in these individuals.

Figure 1:
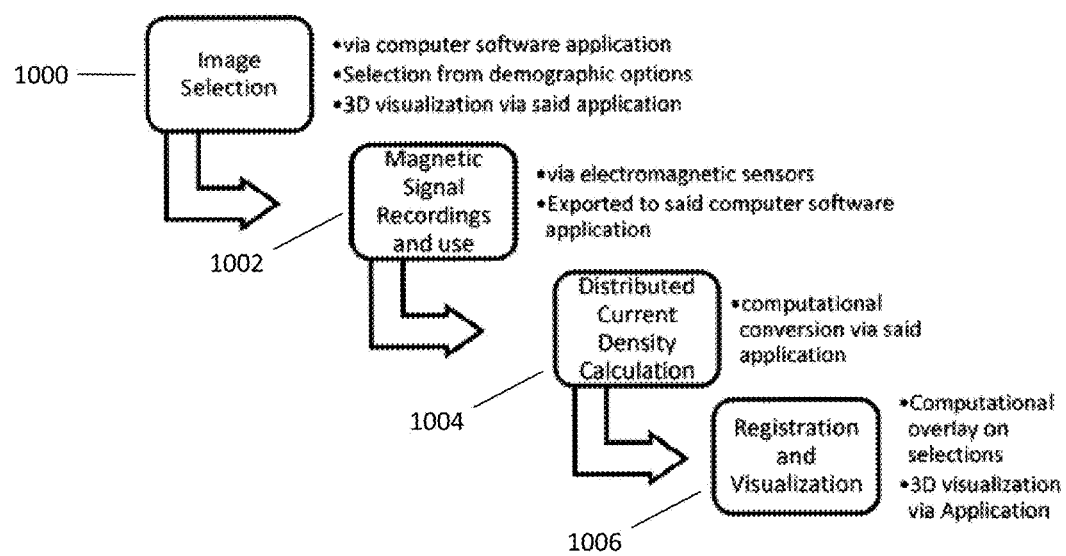
FIG. 1 exemplifies a schematic representation of the steps of an embodiment of the organ evaluation method.

FIG. 1 exemplifies a schematic representation of the steps of evaluating the organ. In a step 1000 an image of the organ is selected. In some embodiments, an image of the organ of an individual is acquired through any suitable visualization technique, visualization techniques include but are not limited to CT scan, MRI, Ultrasound, angiogram, nuclear scan, X-ray, and fluoroscopy. In some embodiments, the image of an organ is demographically matched to the organ of the individual whose organ is evaluated. The demographically matched organ is matched to the organ of the individual whose organ is being evaluated based on a matching of features such as demographic and/or clinical features. Alternatively or additionally, a three dimensional image of the organ of the individual being evaluated is constructed from, for example, one or more two dimensional images of the organ of the individual.

In some embodiments, one or more two dimensional images of an organ are used to generate a three dimensional image of the organ using software configured to import one or more two dimensional images of the organ and use them to construct a three dimensional image of the organ based on the one or more two dimensional images. Two dimensional images are imported from a computer, storage medium, network, or cloud, wherein said two dimensional images may be in a variety of file formats. These two dimensional images may comprise, for example, slices of an organ. These two dimensional images may comprise, for example, different views of an organ, as in, for example, AP, oblique, and lateral X-ray images.

Once obtained, these two dimensional images are characterized. In some embodiments, an image is characterized with respect to the imaging modality (i.e. X-ray, CT, etc.). In some embodiments, an image is characterized in terms of the type of image that is acquired (i.e. a chest x-ray, abdominal x-ray, abdominal CT). In some embodiments, an image is characterized in terms of its quality. Further, the obtained images are transformed into maps of boundary points. In some embodiments, the boundary points represent the borders or outlines of an organ. In some embodiments, the boundary points represent a border or outline of a slice or portion of an organ. In some embodiments, successive slices or views of an organ with given parameters of slice thickness and/or orientations in space are oriented in three dimensional space and then joined to create a computer rendered mesh of the geometry of the organ for which the two dimensional images were obtained.

Segmentation of organ location in terms of sensed data associated with an organ is further performed. Because the anatomical location not occupied by an organ does not generate an electromagnetic field, segmentation is achieved by identifying and segmenting locations with and without electromagnetic measurements. Segmentation thus aids in the identification of an organ within an image that contains the organ as well as other structures by identifying and segmenting regions from which measurements are sensed and regions from which they are not.

The devices, systems, media, and methods described herein also include a registration process, wherein the registration process comprises the overlaying of sensed data associated with an organ (e.g., electrical currents) on an organ template geometry. When segmentation has been applied in response to sensed data associated with an organ the organ geometry of an individual is identified and one or more geometric features are recognized to register the individual's measurements to an organ template geometry. In some embodiments, segmentation and registration are combined into a single process. In some embodiments, segmentation is not performed, and the measurement data is used to register to a template organ.

Alternatively, a three dimensional image or template of an organ or organ structure may be generated by pixel intensity gradient analysis. Pixels in a two dimensional image may be mapped in accordance with their intensity which corresponds to degree of absorbance of an x-ray beam. The organ tissue will typically absorb a transmitted X-ray beam to a larger degree than any surrounding empty space around the organ. The contrast between the high intensity pixels at the border of the image of the organ with the surrounding empty tissue space (which will comprise relatively low intensity pixels) defines the edges of the organ. Once the edges of the organ are mapped out, one or more additional two dimensional images of the same organ are acquired and analyzed in the same way. Results of the pixel intensity analysis of the two or more images are compared and combined to generate voxels and in this way multiple two dimensional images of the same organs may then be used to generate three dimensional volumes based on the one or more pixel intensity maps generated.

Alternatively or additionally, a two or three dimensional image of an organ is constructed based on the sensed data associated with an organ for the organ being evaluated. For example, input magnetic field parameters linked to spatial collection points are filtered using electronic spatial filters (e.g., recursively updated gram matrix) which utilizes known cardiac conduction patterns to numerically estimate the boundaries of electrical flow, thereby determining the shape of the organ, wherein the accuracy is a function of the number of sampling points and the parameters of the conduction model being used.

The devices, systems, media, and methods described herein are configured to combine an anatomically correct representation of an organ, comprising an image or reconstruction of an organ of said individual or with an image of an organ demographically matched to the individual, with sensed data associated with an organ (e.g. current vector and/or current density data) in order to generate a current density and/or current vector map of the organ. The current density and/or current vector map of the organ displays one or more current vectors and one or more current densities associated with one or more anatomical locations of the organ.

In a step 1002, magnetic signal recording and use comprises sensing data associated with an organ using, for example, one or more sensors. In some embodiments, the sensed data associated with an organ, which is sensed by the one or more electromagnetic sensors, comprises a magnetic field associated with an organ. In some embodiments, sensed data associated with an organ comprises current or one or more current vectors.

The devices, systems, media, and methods described herein are configured to sense a magnetic field associated with an organ and translate that data to one or more current vectors of the organ, wherein the one or more current vectors comprise current density and/or flow through the tissue of the organ being evaluated. The one or more sensors comprise one or more electromagnetic sensors.

In a step 1004, sensed data associated with an organ comprising distributed current magnetic field data is converted to current vector data. Alternatively or additionally, current vector data from the organ being evaluated is directly sensed.

In a step 1006, registration and visualization occurs. Registration and visualization comprises overlaying sensed data associated with an organ on top of an image of said organ or an image of a demographically matched organ. As described, in some embodiments, the sensed data associated with an organ comprises magnetic field data, which is converted to one or more current vectors that correspond to current density and/or current flow through the tissue of an organ. The sensed data associated with an organ is localized to a specific anatomical location on the organ and is overlaid on the specific anatomical location on the image of the organ associated with said data so that there is a direct correspondence between the sensed data associated with an organ and the anatomical location on the organ to which the data was localized.

Described herein are devices, systems, media and methods configured to generate or construct a visualization of anatomical electrical activity for an organ of an individual. The devices, systems, media, and methods are further configured to interpret and/or integrate vector-spatial data using computational output and visualization through a computer software application which displays and outputs this data in the context of human anatomy through magnetic conversion and subsequent registration with anatomical data.

II. Organ Evaluation Systems

Figure 2:
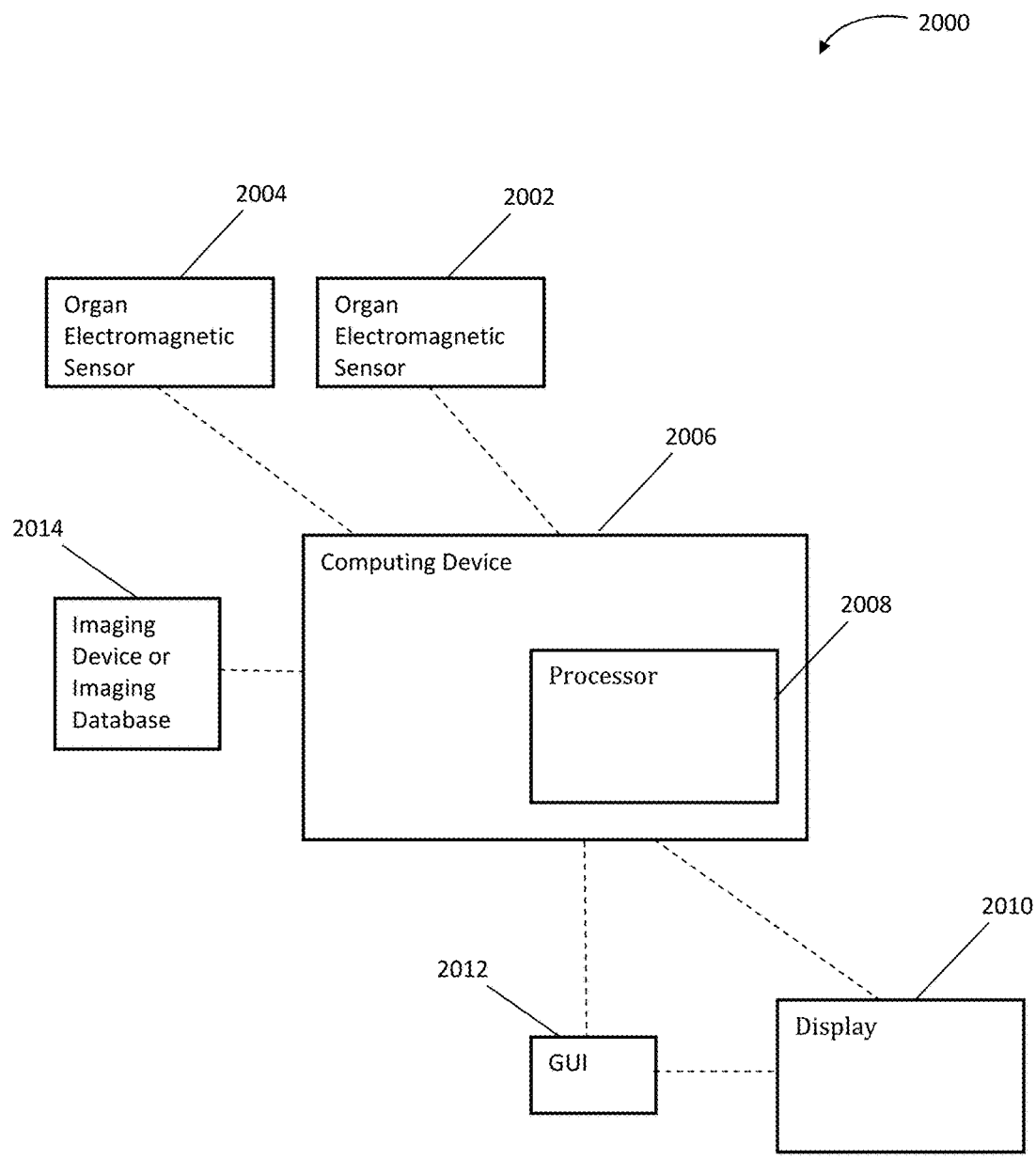
FIG. 2 exemplifies an exemplary embodiment of system for evaluating an organ of an individual.

FIG. 2 exemplifies an exemplary embodiment of system 2000 for evaluating an organ of an individual. A computational backend environment, for example, comprises a computing device 2006, a processor 2008, graphical user interface 2012 (GUI), and a display 2010. Anatomical data is received from an external source 2002, 2004, spanning a plurality of file formats, where the input parameters are combined to visualize and output current density and/or current flow activity having ampere-based units displayed in the spatial context of the heart or other organ anatomy using display 2010.

Devices, systems, media, and methods described herein are useful in the evaluation of current density and/or current flow of an organ in order to produce a two or three dimensional representation of the same, for various animal and human organs using magnetic field analysis. The two or three dimensional representation may be used for the purpose of diagnosing abnormalities or guiding clinical treatment of the same.

The computational backend environment includes a visualization application. A visualization application of the computational backend environment produces, for example, a visual two or three dimensional or four dimensional (i.e., three dimensional plus time) or other rendering of an electroanatomical model of the organ in combination with a user interface 2012 through which processing may occur. In some embodiments, the interface 2012 is configured to provide a user with the ability to manipulate a displayed two or three dimensional image of an organ as well as a two or three dimensional map overlay as described herein. In some embodiment, the interface 2012 is configured to provide a user to further segment or section the organ so that slices of the organ may be viewed and manipulated on the screen. For example, user interface 2012 is configured to allow a user to take slices of variable thickness through a heart to view an endocardial layer. Such embodiments are configured for a user to, for example, view a current density or current vector map overlaying the endocardium of the heart at different selectable depths.

In the backend, three dimensional data can be rendered and manipulated using various methods. In this regard, the computational backend environment can be manipulated to quantify sensed data associated with an organ such as electrophysiological data in a way which allows for diagnosis and/or output of treatment options based on the visualization of distributed current vectors of the organ overlaid on a two or three dimensional geometry of the organ. For example, distributed current vectors of a heart may be overlaid on a two or three dimensional geometry of the heart.

As shown, one or more organ electromagnetic sensors 2002 and 2004 are configured to be positioned external to the body of an animal or human individual and sense data associated with an organ of said individual. The sensed data may comprise magnetic field data associated with an organ. For example, the heart of an individual conducts an electrical current through the myocardial tissue of said heart during normal physiologic function which generates an associated magnetic field that is sensed by the one or more organ electromagnetic sensors 2002 and 2004.

The one or more organ electromagnetic sensors 2002 and 2004 are configured to communicate with a computing device 2006. Such communication may be through wireless or hardwired connections between the organ electromagnetic sensors 2002 and 2004 and the computing device 2006. The devices, systems, media, and methods described herein may comprise an electromagnetic signal acquisition module or step. An electromagnetic signal acquisition module or step is configured to receive a signal transmitted from one or more sensors.

The organ electromagnetic sensors 2002 and 2004 are networked to cooperate in sensing signals, wherein one or more organ electromagnetic sensors 2002 and 2004 are both networked with each other as well as networked with a computing device 2006.

Non-limiting examples of sensed measurement types sensed by said organ electromagnetic sensor comprise a magnetic field, an electrical current, an oscillation/rotation/spinning frequency, a spatial frequency, or a gradient. Measurement units comprise Ampere, Volt, Gauss, Hertz, or Seconds. A measurement magnitude may comprise a scalar, an amplitude, or a length. A measurement direction/orientation and/or magnitude comprises a vector, and a measurement location comprises an x-y-z coordinate with respect to a defined origin, or a combination thereof. In some embodiments, a plurality of sensed data associated with an organ.

Various organ electromagnetic sensor designs are possible. For example, a sensor may be configured to sense a snap-shot response, or a sequence of snap-shop responses, or a continuous analog response over time. In some embodiments, a plurality of sensors collectively acquires a plurality of responses. In additional embodiments, synthesis of a plurality of responses reconstructs activities of an organ. Furthermore, analyzing the responses associated with the organ or based on additional knowledge/databases reveals electrical/molecular/mechanical/chemical activities in the organ. Non-limiting examples of sensors suitable for use with the devices, systems, media, and methods described herein include electromagnetic sensors such as Superconducting Quantum Interference Devices (SQUIDs) and Atomic Magnetometers. A Magnetometer is configured to sense a Magnetocardiogram of a heart. A Magnetometer may be further configured to sense magnetic field data relating to other organs.

In some cases, an electromagnetic field comprises a purely magnetic field or a purely electrical field. In some embodiments, a sensed electromagnetic field is oriented to a point or a plane of interest associated with an organ. One or more electromagnetic fields associated with an organ may be sensed in order to locate a specific portion (e.g., a point, a plane, a three dimensional region, etc.) of said organ.

While FIG. 2 exemplifies two organ electromagnetic sensors 2002 and 2004 in communication with a computing device 2006, it should be understood that multiple configurations of sensors and computing devices are suitable for use with the devices, systems, media, and methods described herein. For example, one organ electromagnetic sensor may be configured to communicate with one computing device. For example, one organ electromagnetic sensor may be configured to communicate with two or more computing devices. For example, one or more organ electromagnetic sensors may be configured to communicate with one or more computing devices. Numerous suitable computing technologies are suitable for use as a computing device 2006 including but not limited to a desktop computer, a laptop computer, a tablet computer, a smartphone, or a smartwatch. A computing device 2006 comprises a processor 2008 through which, for example, magnetic field data sensed by one or more organ electromagnetic sensors is translated to current vector data and/or current density data associated with specific anatomic locations of said organ. A computing 2006 either comprises or is coupled with a GUI 2012 that allows a user to analyze, control, and interact with the data sensed by the organ electromagnetic sensors 2002 and 2004 and/or image data and or translated data. A computing device 2006 either comprises or is coupled with a display 2010 that is configured to display the current density and/or current vector map of the organ being evaluated. The display and/or the GUI 2012 may be coupled directly with each other, directly with the computing device 2010, or one or both may be remotely located.

The system further comprises a connection to either an imaging device or an imaging database 2014. Non-limiting examples of imaging devices 2014 suitable for use with the systems, devices, media, and methods described herein include a CT scanner, an MRI, an ultrasound, a fluoroscope, a nuclear scanner, an X-ray, and any other device configured to generate an anatomical image or representation of an organ. An imaging database 2014 comprises a database of images from any one or more of the imaging devices 2014. In some embodiments, an image or representation of an organ of a subject or a demographically matched image of an organ is transmitted from the imaging device or imaging database 2014 to the computing device 2006 of system 2000.

In an alternative embodiment, a representation of an organ being evaluated is generated based on the data sensed from organ sensors 2002 and 2004. Computing device 2006 is configured to combine current vector and/or current density data translated by said processor 2008 from the received magnetic field data and combine the current vector and/or current density data with an image or representation of an organ by, for example, overlaying the current vector and/or current density data over the received image or representation of an organ.

Alternatively computing device 2006 generates a visual representation of an organ being evaluated by visually displaying current densities and/or current vectors translated from said sensed magnetic field data in an arrangement that represents the anatomical configuration of the organ being sensed. The generated overlay image or representative image comprises a map wherein one or more current vectors and/or current density are represented by different icons positioned in an anatomical position which the icons are associated with. For example, in said generated map, a current density of a left ventricle of a heart is positioned in a location corresponding to the anatomic location of the left ventricle in space. In this way, a user may look at a display map and visually identify one or more current vectors and/or current densities associated with various anatomic locations of an organ. Said generated map is configured to be displayed as either a two or three dimensional map on display 2010. A GUI 2012 is configured to provide a user the ability to manipulate the generated map by, for example, moving the generated map to view different angles or locations. A GUI 2012 is configured to provide a user the ability to examine slices through an organ so that, for example, the user may view one or more current vectors and/or current densities associated with tissue within the organ.

Described herein are systems comprising one or more electromagnetic sensor devices and at least one processor configured to execute instructions from a software application. Said systems are configured to obtain and provide electrical activity data as a function of electromagnetic activity in response to measurements (e.g., electrical/magnetic data values) for an organ (for example a heart) as an output of said sensor and input of said processor, wherein said sensed data associated with an organ includes a representative series of recordings defining distributed electromagnetic activity (such as cardiac electromagnetic data) in three dimensional vector space during a specified time period and specified time period markers for the aforementioned recordings. Said system utilizes organ tissue anatomical data (for example, heart anatomical data), wherein said data includes a plurality of data files providing electronic three dimensional or other mappings of organ geometry (such as heart geometry) embodied on non-volatile memory, and processes by computer processor the input magnetic activity data provided by a sensor and the input organ tissue anatomical data (e.g., the heart anatomical data). Processing includes calculating a plurality of distributed, spatially accurate electrical current vectors (with units of amperes or other suitable units) in two or three dimensional space and uniquely identifying and outputting them in reference to anatomical structures found within an organ anatomic geometry. In some embodiments, an organ evaluation device, system, medium, or method also displays both electrical current vectors and anatomical tissue (e.g. heart or other organ) or other anatomic sensed data associated with an organ simultaneously through the process of image registration, wherein said registration involves functional overlay of three dimensional anatomical reconstruction with electroanatomical data provided by computational processing. Non-limiting examples of computing devices suitable for use with the systems, devices, media, and methods described herein includes a smartphone, a smartwatch, a laptop computer, a desktop computer, and a tablet computer.

III. Organ Evaluation Process

Devices, systems, media, and methods described herein are configured to generate organ evaluations (for example, heart evaluations) and enable measured activity of the current density and/or current flow of the organ through transformation of sensed data associated with an organ comprising sensed electromagnetic field data generated by the organ. For example, the devices, systems, media, and methods described herein are configured to generate cardiac evaluations and enable measured activity of whole-heart current density and/or current flow through transformation of sensed electromagnetic field data generated by the heart and specifically by current passing through the myocardium of the heart.

The transformation of sensed data associated with an organ comprising magnetic field data associated with an organ comprises the solution of an inverse problem, wherein the solution involves the utilization of Maxwell's Laws of Electromagnetism to relate magnetic measurements, collected by electromagnetic sensors, and electrical current measurements. Determining the current density and/or current flow and/or electrical activity involves solving an implementation of an inverse problem using Maxwell's Electromagnetic Equations with explicit attention to spatial location and known geometries of the organ, for example, the heart. In doing so, vector calculus and systems of partial differential equations are utilized to uniquely define the organ (for example, the heart) in a two or three dimensional context, while solving for current using magnetic field and these defined spatial parameters to produce current vectors for the entire spatial representation of the organ (for example, the heart). Utilizing the Biot-Savart Law, the inverse problem as defined by its systems of partial differential equations are solved numerically via finite element methodologies which allow input data to be related to electrical current behavior, as limited by the structure and physically relevant constraints of the organ's (for example, the heart's) electromechanics. In this way, algorithmic input and processing of data are used to generate information about current flow in the organ (for example, the heart).

One or more mathematical transforms and or projections are used to transform raw measurements sensed from an organ (e.g. a heart) relating to sensed data associated with an organ. For example, electromagnetic data associated with an organ is measured in a frequency space, and a Fourier transform is employed to infer corresponding responses in a spatial space or in a space of electrical currents. For instance, a Radon transform or a Penrose transform is used for synthesizing responses in a three dimensional space. Via the aforementioned finite element methodologies, Fourier transforms and appropriate analogues are used to spatially transform the coordinates of the input source to the calculated current source described above.

Measurement of an electromagnetic field or a plurality of electromagnetic fields associated with an organ allows measurement of a property of an entire organ or a portion of an organ. For example, a measurement of an electromagnetic field or electromagnetic fields associated with an organ allows measurement of a current density and/or current flow associated with said organ or a segment of said organ. Non limiting examples of other measurements that may be measured by measuring the electromagnetic field associated with an organ include an energy state associated with said organ, a polarization state associated with said organ, a polar orientation associated with said organ, an oscillation frequency associated with said organ, a rotation/spinning frequency or speed associated with said organ, an electrical current associated with said organ, a an electrical voltage associated with said organ, a change in mass associated with said organ, a presence of or change in a mechanical force associated with said organ, a presence of or change chemical force associated with said organ, or any combination thereof. Measurement of an electromagnetic field or a plurality of electromagnetic fields associated with an organ also allows measurement of temporal organ physiology (e.g., a myocardial movement during a cardiac cycle, a brain functioning over time, etc.).

Device, system, media, or method described herein comprise a data integration module, or use of the same. In some embodiments, sensed data associated with an organ is integrated with other information, e.g., organ geometry, organ physiology. In some embodiments, measurements of an individual's cardiac (or other) electrical activity responding to magnetic field excitation are collected over time through a network of electromagnetic sensors, and anatomical heart (or other) geometry data is imported from one of a plurality of file formats relating to a patient. In some embodiments, processed measurements of electrical activity that create distributed current vectors and/or current densities in units of amperes or other suitable units, are overlaid on the imported heart (or other organ) geometry in a representative manner with real time context to demonstrate whole-heart or whole-organ vector map and/or current density.

Integrating sensed data associated with an organ (e.g., electrical currents) with other types of data may comprise a synchronization process. For example, overlying temporal sensed data associated with an organ on a template of a myocardial geometry includes synchronizing a cardiac cycle. Thus one or more images are time synched with a cardiac cycle as well as with the corresponding sensed magnetic field data. In some embodiments, the time synched images are displayed in a movie or streaming format such that a time synched current density or current vector map is overlayed on the one or more streaming images so that the map(s) are viewed over time through the cardiac cycle. Similar time synching through integration of data is also applied to other organs wherein a change in the current density or current vector map is displayed over time.

In some embodiments, an organ evaluation device, system, medium, or method receives sensed data associated with an organ (e.g., magnetic data) from an individual which data are integrated with a pre-rendered and demographically compatible two or three dimensional organ image model within a computational backend environment where the input parameters are combined to visualize two or three dimensional electroanatomical images, without the need for individual-specific images. The computational backend environment then evaluates said images for potentially ectopic electrophysiological activity, particularly as it relates to triaging chest pain in the emergency room. In this regard, the computational backend environment can evaluate magnetic field data over a cardiac cycle in a way which allows for an accurate two or three dimensional visualization and output of an urgency index depicting the degree of urgency or lack thereof, for said patient. For example, an individual experiencing an acute onset of arrhythmia can be evaluated immediately during the period of arrhythmia even if no image of the individual's organ is available by using an image of an organ of a demographically matched individual that is, for example, matched to the individual being evaluated by factors such as demographic, biometric, or medical history related factors.

An organ evaluation device, system, medium, or method is configured to sense data associated with an organ (e.g., electrical currents, electrical current vectors, etc.) and electronically imported anatomical cardiac tissue image data, which provides for joint registration of electrical and anatomical data based on landmark and structure identification. Registration refers to data-skin overlay of a two or three dimensional image such that quantitative data is displayed qualitatively with a plurality of color gradients bound to certain quantitative scales in two or three dimensional space, with particular relation to said structures and landmarks. In some embodiments, an organ evaluation device, system, medium, or method includes predetermined embodied anatomical cardiac (or other organ) tissue that is selection based on a plurality of indicated demographic and lifestyle factors; wherein the demographics and lifestyle factors may include but are not limited to factors of health status, age, gender, a priori illness, inflammation, scar tissue, diet, smoking, and substance use. In some embodiments, the process of selection of the data involves external selection as a function of the preceding demographic factors.

An organ evaluation device, system, medium, or method may be further configured to analyze one or more electromagnetic fields associated with an organ to provide a comprehensive assessment of the functional electrophysiology of said anatomical organ. The sensed electromagnetic field associated with said organ may be further associated with one or more other types of physiological measurements (e.g., EEG, ECG) to provide a comprehensive assessment of the functional electrophysiology of an anatomical organ. For example, an organ evaluating system provides a comprehensive assessment of functional cardiac electrophysiology, and said assessment further comprises one or more biometric measurements. Non-limiting examples of biometric data includes a heart rate, a heart variability, a blood pressure, a temperature, and an electrocardiogram. Similarly, an evaluation of any organ may further comprise one or more sensed biometric measurements.

A computer implemented method comprises an evaluation through detecting, localizing and quantifying arrhythmogenic substrates in the heart.

A device, system, medium, and or method for visualizing two or three dimensional electroanatomical images may be configured to comprise cardiac imaging data and functional magnetocardiogram data associated with an cardiac of an individual. An organ evaluating system is configured to provide a two or three dimensional map of the electrical current that travels through an organ. The electrical current that travels through an organ is mapped into a two or three dimensional representation of the organ from which the current data was sensed. Alternatively or additionally, the electrical current that travels through an organ is mapped into a three dimensional representation of the organ from which the electrical current data was sensed. For example, in some embodiments, an cardiac evaluating device, system, medium, or method identifies an abnormal current pattern in an area of a heart of an individual with an arrhythmia. In additional embodiments, the abnormal current along with the current pattern of the entire heart is mapped in either a two or three dimensional representation of the heart of the individual so that the current abnormality is localized to a specific area of the heart. In further embodiments, the arrhythmia type may be, for example, identified as a localized arrhythmia type amenable to treatment with catheter ablation, and the accurate localization of the area of abnormal current flow allows for successful and accurate ablation.

An organ evaluation device, system, medium, or method generates a visual representation of an evaluation of an organ, which is used by a physician or health care professional to diagnose electrophysiological disorders or lack thereof in the heart, or organ of interest, by identifying the existence or lack thereof, of patterns of current abnormality and regions of inactivity or arrhythmia, and enabling a user to recognize the existence or lack thereof relating to patterns of current abnormality and locate regions of inactivity or arrhythmia.

An organ evaluation device, system, medium, or method may be configured to output distributed current vectors and two and three dimensional mapping of heart geometry or other organ geometry for an individual. In some embodiments, an organ evaluation device provides a software application and a user interface. An organ evaluation device, system, medium, or method may be configured to import and utilize two dimensional or three dimensional data embodied in a plurality of various suitable file types relating to anatomical geometry, and provides a system for the importation and utilization of sensed data associated with an organ (e.g., magnetic field data) provided by one or more sensors, such as, for example, one or more electromagnetic sensors. In some embodiments, an organ evaluation device, system, medium, or method further provides an electronic visual display software application, the display showing both magnetic amplitude waveforms and distribution vectors, and interpreting by said application components of three dimensional anatomical distributed current models through a spatially oriented user interface, in which a user is capable of manipulating the rendered object through aforementioned GUI to alter field of view and enlarge or shrink the object. In some embodiments, a user interface allows for manual manipulation through said user interface of spatial observation for the individual, and wherein said manipulation includes alteration of said image through said computational backend and alteration includes manipulation of nonstructural qualitative factors including but not limited to color, position, and opacity. In some embodiments, accumulated electrical vector data identifies unique spatial landmarks and structures such as but not limited to the septum, valves, or conducting nodes in the heart. The specific landmarks may be different in different embodiments, depending on the organ of interest.

An organ evaluation device, system, medium, or method for quantifying and displaying distributed cardiac current vector activity for an individual, configures electrical activity data provided by a processor, wherein the step of configuring includes determining the file format of the data provided.

An organ evaluation device, system, medium, or method for quantifying and displaying cardiac current density activity for an individual calculates distributed cardiac current vector activity in dynamic, time-based parameters as distributed current density changes in time, in both magnitude and spatial direction during the course of both regular and irregular heart rhythm.

An organ evaluation device, system, medium, or method configured for quantifying and displaying distributed cardiac current density activity for an individual additionally provides an activity database of current density output having baseline activity recordings. In some embodiments, an organ evaluation device, system, medium, or method further interprets sensed data associated with an organ comprising sensed magnetic field data and externally selected anatomical data, wherein interpretation comprises comparing provided externally selected anatomical data with database baseline activity recordings, and evaluating by the comparison of activity as a function of risk assessment, where greater deviations from accepted baseline activity are indicated as higher risk factors and are directly related.

An organ evaluation device, system, medium, or method may be configured to sense a current density of an organ and/or a current flow through an organ. The current flow may comprise an electrical current flow. An electrical current density and/or current flow may be represented by one or more current vectors representing the direction and magnitude of current flow. One or more current vectors may be mapped in relation to the anatomical area of an organ wherein the one or more current vectors are measured. For example, a current vector sensed within the ventricle of a heart of an individual is mapped in that anatomical location within a representation of the heart of the individual.

An organ evaluation device, system, medium, or method may be configured to sense an electrical field around an organ of an individual. An electrical field around an organ is measured with one or more sensors. In some embodiments, electrical field data sensed from an organ of an individual is translated to a current flow represented by current vectors, which represent flow of electrical current through the tissue of said organ.

An organ evaluation device, system, medium, or method may be configured to generate an anatomical image of the organ evaluated. Alternatively or additionally, the anatomical image comprises an overlay of a current vector map of the organ over either a two dimensional or three dimensional image of the organ. The two or three dimensional image of the organ may, for example, comprise a CT scan of the organ. The two or three dimensional image of the organ may, for example, comprise an MRI of the organ. The two or three dimensional image of the organ may, for example, comprise a fluoroscopic or X-ray image of the organ.

In some embodiments, an organ evaluation device, system, medium, or method evaluates data from an individual in light of or in combination with patient demographic data. In some embodiments, organ related data is integrated in a computational backend environment with inbuilt anatomical data where the input measurements may be combined with the selected anatomical parameters to visualize and output current density activity having, for example, ampere or other units displayed in the spatial context of the anatomy of an organ, such as, for example, heart anatomy. In some embodiments, the computational backend environment includes a visualization application, which in certain embodiments further comprises a user interface through which processing may occur. In some embodiments, in the backend, three dimensional data is generated and can be rendered and manipulated. In additional embodiments, the computational backend environment quantifies electrophysiological data in a way which allows for an accurate diagnosis and output of treatment options for medical patients based on the display and visualization of distributed current vectors overlay on three dimensional cardiac geometry. In some embodiments, demographic data of an individual or of one or more other individuals are combined with the magnetic data to generate an evaluation of the organ of said individual. Demographic data may comprise, for example, age, gender, height, and weight data. Demographic data may comprise, for example, anatomical data such as for example the size, shape, and weight of an organ. In some embodiments, the magnetic field data associated with an organ of an individual is combined with, for example, the organ size, shape, and weight of another individual who is age, gender, and weight matched to said individual being evaluated.

Magnetic field measurements are processed to electrical activity data to create distributed current vectors in units of amperes or other units. In some embodiments, one or more current vectors are overlaid on a selected organ geometry in a representative manner with real time context to demonstrate whole-organ current density. Various techniques may be used to create the overlay. The measurements of one or more distributed current vectors are calculated and represented by treatment of each of a plurality of spatial points as individual contributors to cardiac current and electrical activity. In some embodiments, the evaluation of a determined distributed current vector activity is performed through a two or three dimensional rendering of an organ of an individual being evaluated. In some embodiments, a three dimensional rendering of an organ of an individual comprises a CT scan or MRI image of the organ. In some embodiments a three dimensional image of an organ of an individual is constructed using one or more two dimensional images of said organ, such as, for example, images obtained through fluoroscopy or X-ray. In some embodiments, a two or three dimensional image of a demographically representative patient is used using the aforementioned software application. In some embodiment, a three dimensional image is generated using one or more two dimensional images.

A device, system, medium, and method for organ evaluation enables visualization of inbuilt organ anatomy, such as, for example, cardiac anatomy with real time context by utilizing a software interface and computer backend to generate an accurate, three dimensional representation of the electrical activity of the entirety of, or at least part of, a heart or other organ. Whole-heart current density is measured and visually represented with a software application and in real time context through joint registration of qualitatively represented current data and either specific or non-specific, representative anatomical data of an individual. As described, cardiac tissue anatomical data is embodied as predetermined anatomical image data that includes unique identifiers of corresponding structures and landmarks, and may be presented in various forms.

Described herein is a computer implemented method for evaluation through detecting, localizing and quantifying localized points of interest or abnormality, in an anatomical organ. The method comprises the steps of providing an electromagnetic sensor device having at least one processor configured to execute instructions from a software application; providing a computer backend having at least one processor configured to execute instructions from a software application having a plurality of inputs and outputs; providing electrical activity data as function of electromagnetic activity in magnetic data values for the anatomical organ tissue as an output of said sensor and input of said backend, wherein said data includes a representative series of recordings defining distributed anatomical organ tissue electromagnetic activity in three dimensional vector space during a specified time period and specified time period markers for the aforementioned recordings; utilizing anatomical data for anatomical organ tissue, wherein said anatomical organ tissue data includes a plurality of data files providing electronic three dimensional mappings of heart geometry embodied on non-volatile memory. The method further includes processing by said computer processor the input magnetic activity data provided by said sensor and input anatomical organ tissue data, wherein the step of processing includes calculating a plurality of distributed, spatially accurate electrical current vectors (with units of amperes) in three dimensional space and uniquely identifying and outputting them in reference to anatomical structures found within said anatomical organ geometry files; and displaying both electrical current vectors and anatomical data simultaneously through the process of image registration, wherein said registration involves functional overlay of three dimensional anatomical reconstruction with electroanatomical data provided by computational processing.

An organ evaluation device, system, medium, or method for detecting, localizing and quantifying arrhythmogenic substrates in a heart or other organ for an individual is provided. The system comprises: an electromagnetic sensor network including an electromagnetic sensor and computer backend having at least one processor and memory, wherein said processor is configured to execute instructions from a software application to cause the electronic device to process electrical activity data for the heart or other organ tissue, wherein said data includes a representative series of recordings defining distributed electrical activity in three dimensional vector space during a specified time period and specified time period markers for the aforementioned recordings, and wherein the step of processing includes calculating a plurality of distributed, spatially accurate vectors with units of electrical current in three dimensional space and uniquely identifying them in reference to anatomical cardiac data, wherein said anatomical cardiac data includes a plurality of data files providing electronic three dimensional mappings of heart geometry embedded on non-volatile memory. Current vector activity is visualized via qualitative representations of numerical values, by means of scales such as color patterns overlaying the rendered anatomical image, also known as electroanatomical registration, to demonstrate current density and/or flow. In this embodiment, the registered image may be manipulated various ways within software to change aspects of the image, such as spatial view, color, and opacity or other chosen qualities. Please refer to FIGS. 3 through 11 for examples of such representations according to various embodiments of the invention.

IV. Exemplary Cardiac Evaluation Displays

Figure 3:
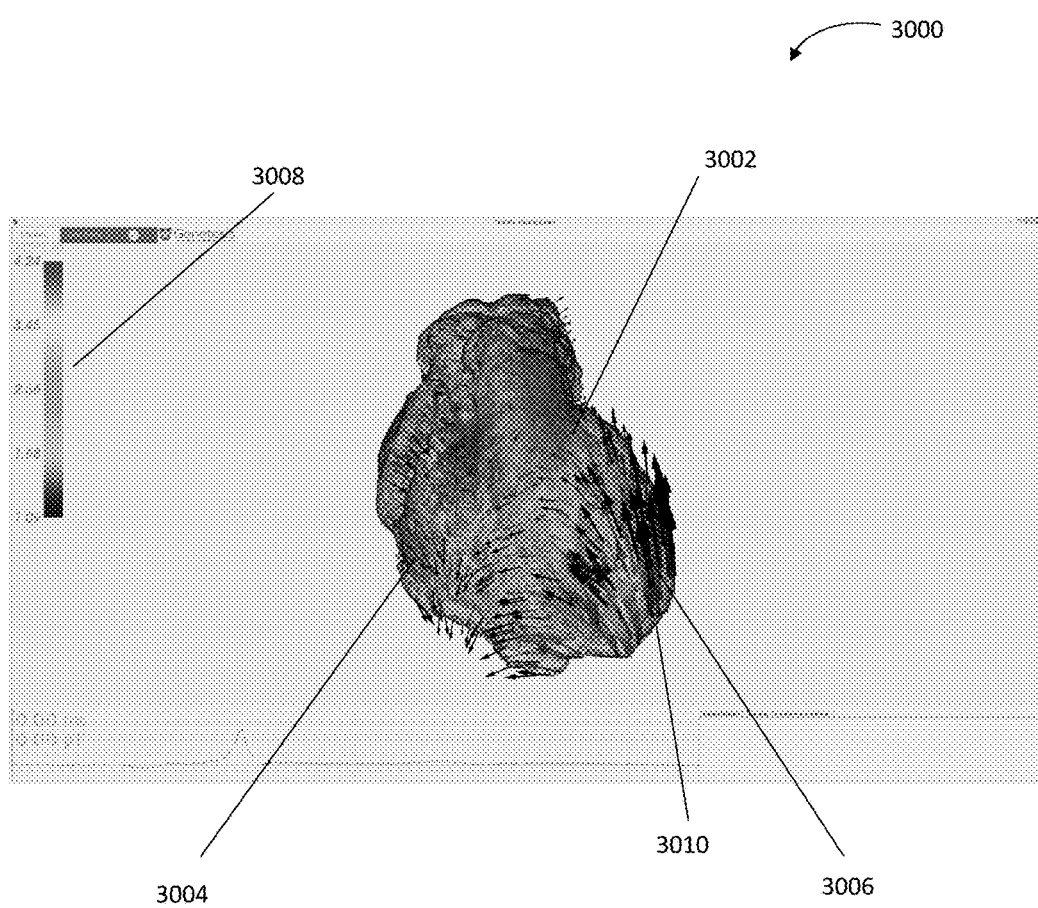
FIG. 3 exemplifies an embodiment of a cardiac evaluation system display showing a current density and current vector map of a heart of an individual comprising of combined functional current data as observed and manipulated in the software application.

FIG. 3 exemplifies an embodiment of a cardiac evaluation system display showing a current density and current vector map of a heart of an individual comprising of combined functional current data as observed and manipulated in the software application. Note here that the distributed current vectors are defined in the context of their magnitudes as points in three dimensional space, wherein the value of the current density in Ampere-based units is displayed using a dynamic color scheme, but other techniques for representing different amperage levels may be used in other embodiments. More specifically, FIG. 3 exemplifies a software screenshot representation 3000 of combined anatomical and functional imaging showing distributed current vectors as arrows on a three dimensional cardiac surface. As shown, the size of an arrow representing a particular current vector is based on the magnitude of current measured by the vector (i.e. a larger arrow represents a larger magnitude of measured current and a smaller arrow represents a smaller magnitude of measured current). The software viewer 3000 allows for localization of arrhythmogenic substrates within either a specific or nonspecific cardiac anatomy. A specific cardiac anatomy comprises an anatomy of an heart of an individual as shown in an image or other representation of the heart of the individual being evaluated. A non-specific cardiac anatomy is an image or other representation of a heart that closely resembles that of the individual being evaluated and is capable of guiding treatment for a physician. Arrhythmogenic substrates may be described as localized points of interest or of abnormality of the heart, but other substrates that are representative of localized points of interest or of abnormality of other organs are used in other embodiments. In addition, while processing, the software implemented method and system may also perform a step of configuring electronic files containing data of current density activity in two or three dimensional space, if such files are in a non-readable file format, to enable the underlying measurements to be extracted and populated into readable file formats. Current density is represented by different colors according to key 3008 which shows a scale of colors corresponding to Amperes of current per unit area. For example, current density 3002 which appears as blue to light blue in color represents an approximate Ampere density value between 1.09 and 1.88 according to key 3008. As shown, current density 3002 is over an anatomical portion of the heart in the shown map corresponding approximately to the left atrium. Similarly, as shown, current densities of multiple colors are shown over region 3004 which according to key 3008 correspond to an Ampere density values between 2.66 and 4.24. As shown, region 3004 corresponds to the left ventricle. Thus, the current density seen in 3004 represents an increased current density in the left ventricle relative to the left atrium and thus typically, in the normal individual, represents the heart in systole, wherein the left ventricle contracts and the left atrium is relatively relaxed. The vectors shown over region 3006 are the largest in magnitude in the map and generally show that the largest magnitude of current, which are directed in a direction from the apex 3010 of the left ventricle upwards along the left ventricle and laterally towards the right side of the heart. Region 3004 shows the current density over the right side of the heart.

Figure 4:
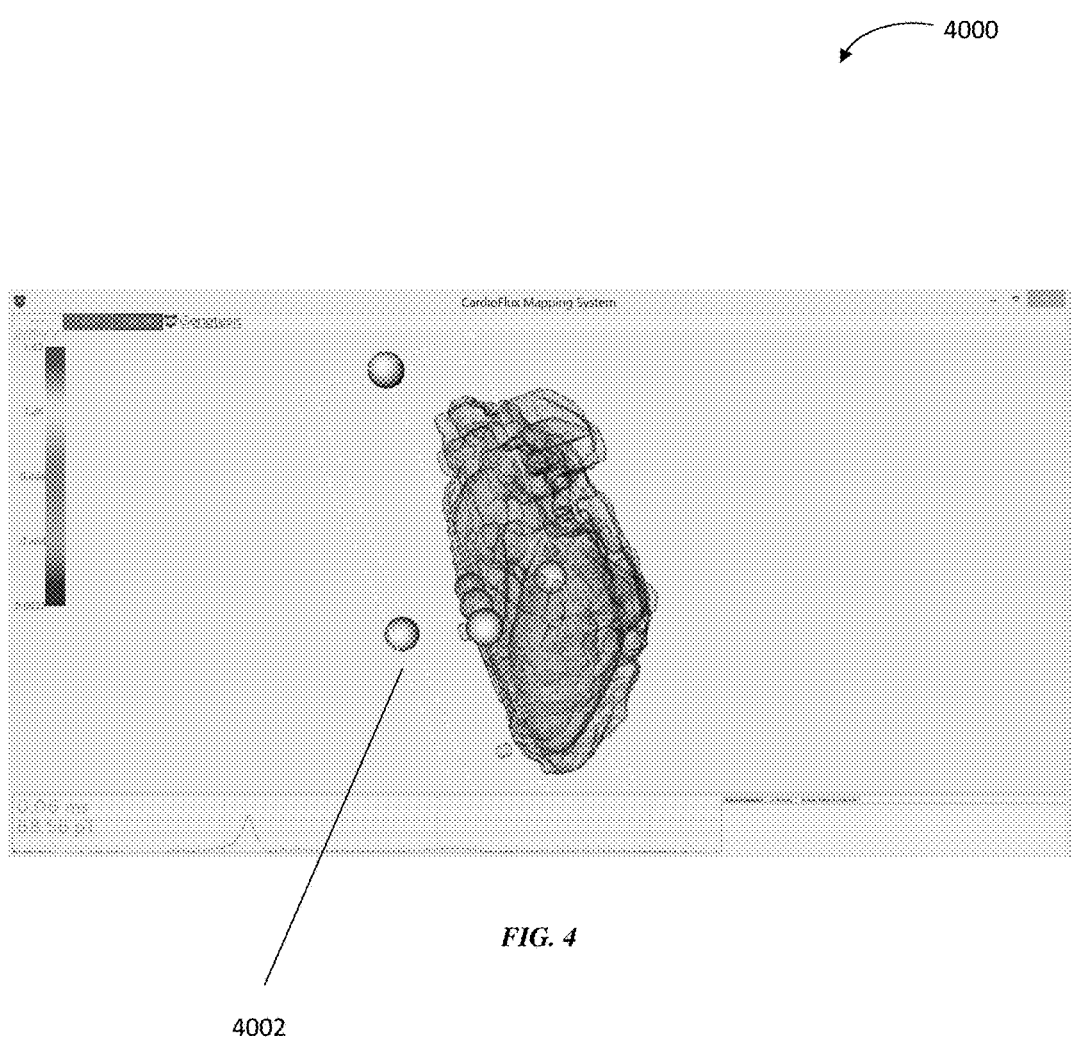
FIG. 4 exemplifies a screenshot of an embodiment of a cardiac evaluation system display showing a current density map of a heart of an individual including an extraction tool.

FIG. 4 exemplifies a screenshot 4000 of an embodiment of a cardiac evaluation system display showing a current density map of a heart of an individual including an extraction tool 4002. An extraction tool 4002 is part of a GUI that is configured to allow a user to obtain desired views of a current density map of an organ such as a heart. For example, as shown in FIG. 4, an extraction tool 4002 provides a user with a view of a section or slice of a myocardium of a heart, thus showing an electric current map through a slice of a heart revealing current density of the sub-surface myocardium.

Figure 5:
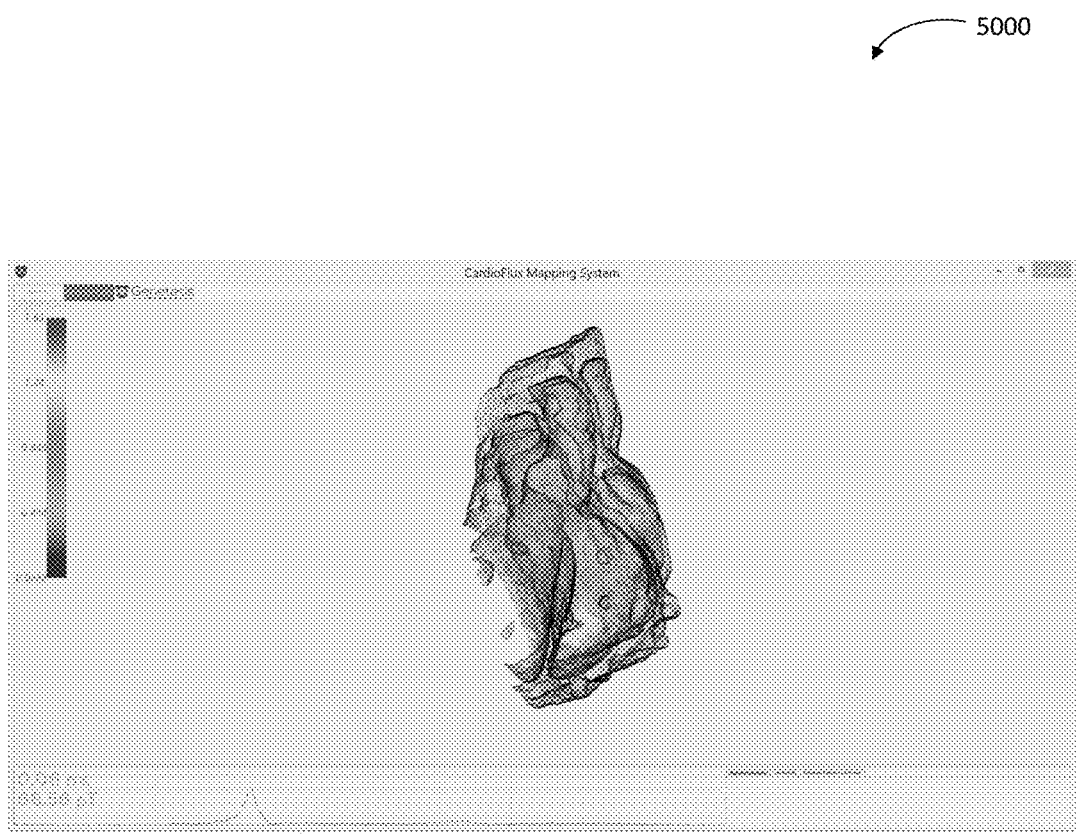
FIG. 5 exemplifies a screenshot of an embodiment of a cardiac evaluation system display showing a cardiac current map comprising an endocardial analysis.

FIG. 5 exemplifies a screenshot 5000 of an embodiment of a cardiac evaluation system display showing a current density map comprising an endocardial analysis. As shown, a cardiac current map of an endocardial portion of a heart of a subject shows a current density map of the sub-surface myocardial tissue of said subject. In this way, the whole heart may be evaluated and not just the superficial myocardial tissue.

Figure 6:
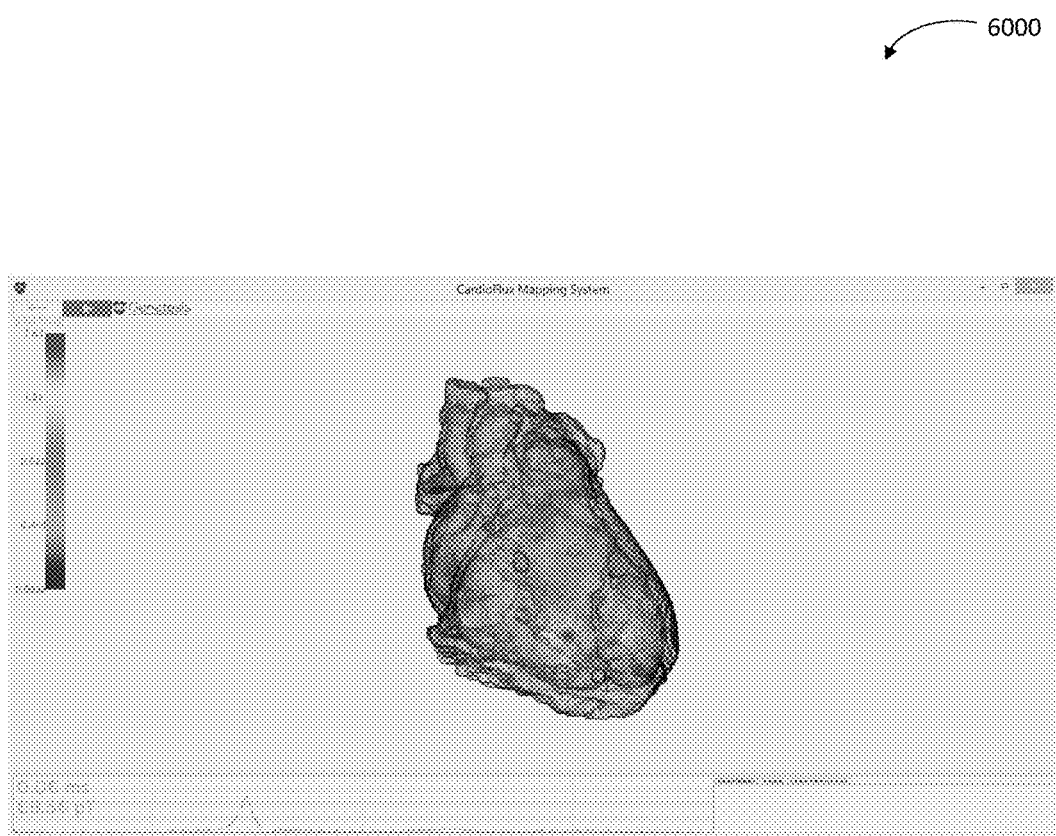
FIG. 6 exemplifies a screenshot of an embodiment of a cardiac evaluation system display showing a wireframe perspective of a cardiac current density map. A wireframe perspective comprises a higher resolution perspective wherein a current density is sensed and displayed over a smaller region of surface of the heart.

FIG. 6 exemplifies a screenshot of an embodiment of a cardiac evaluation system display showing a wireframe perspective of a current density map of a heart 6000. A wireframe perspective comprises a higher resolution perspective wherein a current density is sensed and displayed over a smaller region of surface of the heart.

Figure 7:
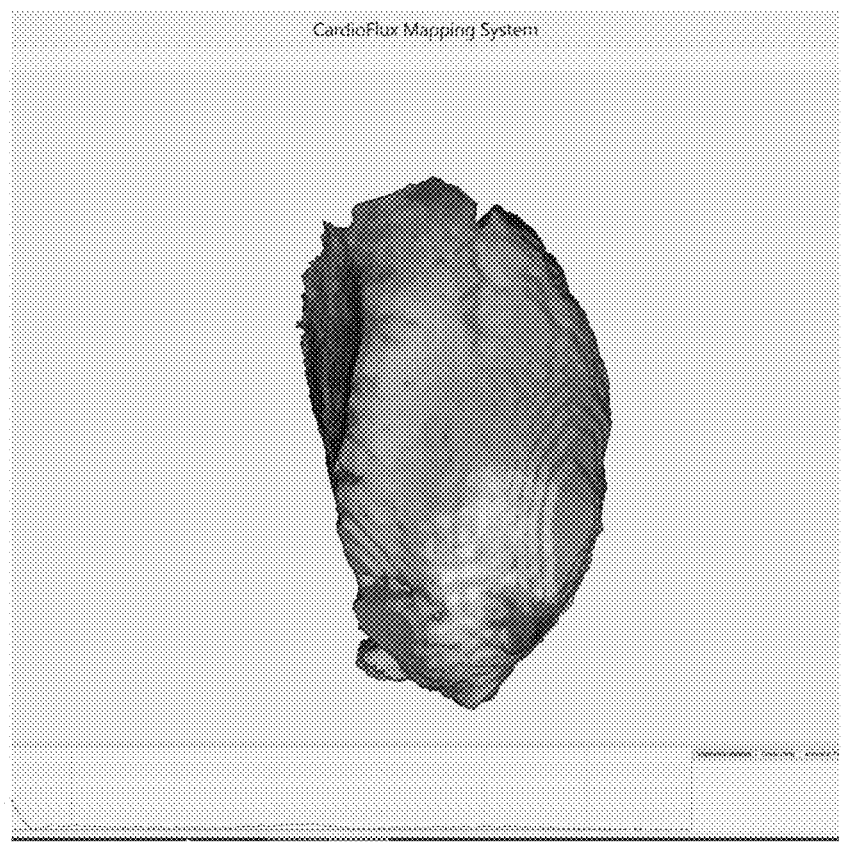
FIG. 7 exemplifies screenshot of an embodiment of a cardiac evaluation system display showing a cardiac current density map of an isolated left ventricle.

FIG. 7 exemplifies a screenshot of an embodiment of a cardiac evaluation system display showing a current density map of an isolated left ventricle 7000. As shown, a portion of the cardiac anatomy may be displayed in isolation so that user may evaluate, for example, a cardiac current density map of a left ventricle of a heart.

Figure 8:
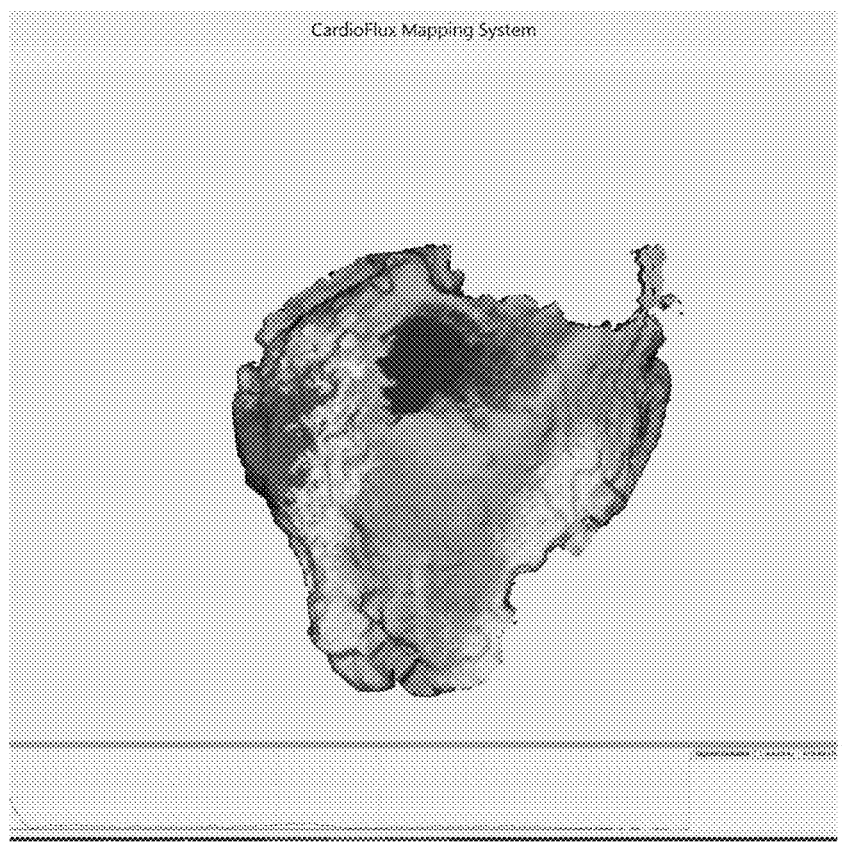
FIG. 8 exemplifies a screenshot of an embodiment of a cardiac evaluation system display showing a cardiac current density map of an isolated right ventricle.

FIG. 8 exemplifies a screenshot of an embodiment of a cardiac evaluation system display showing a current density map of an isolated right ventricle 8000. As shown, a portion of the cardiac anatomy may be displayed in isolation so that user may evaluate, for example, a cardiac current density map of a right ventricle of a heart.

Figure 9:
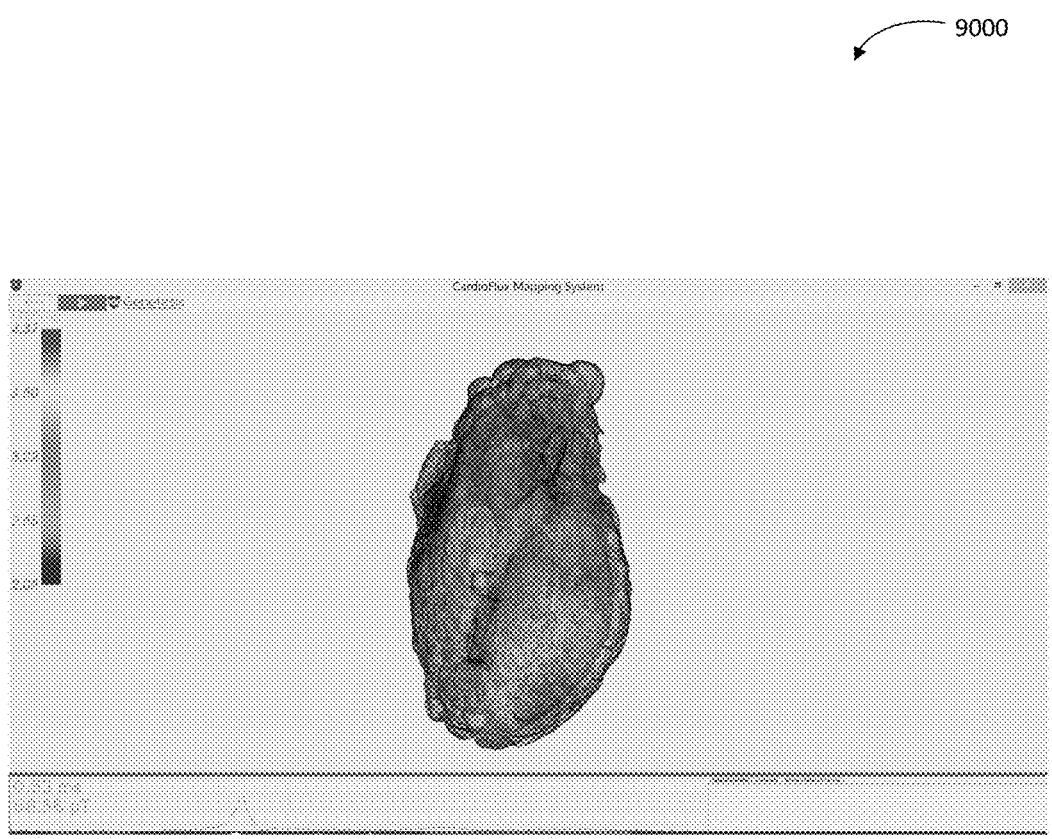
FIG. 9 exemplifies a screenshot of an embodiment of a cardiac evaluation system display showing a cardiac current density map of a heart during a QRS complex of an ECG. As shown, a cardiac current density map may be combined with ECG data to generate an evaluation of a heart of an individual, wherein a cardiac current density map is generated while the individual has an ECG measured.

FIG. 9 exemplifies a screenshot of an embodiment of a cardiac evaluation system display showing a current map of a heart during a QRS complex of an ECG 9000. As shown, a cardiac current density map may be combined with ECG data to generate an evaluation of a heart of an individual, wherein a cardiac current density map is generated while the individual has an ECG measured.

Figure 10:
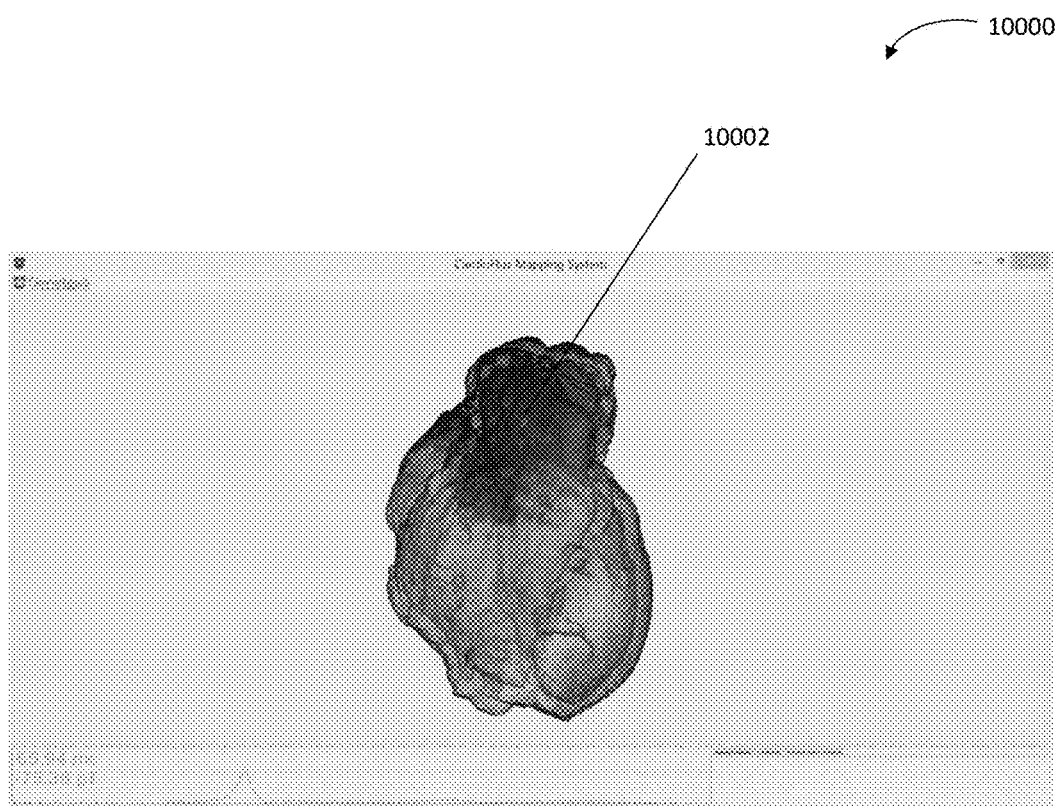
FIG. 10 exemplifies as screenshot of an embodiment of a cardiac evaluation system display showing an embodiment of a dynamic current density of an individual in atrial fibrillation.

FIG. 10 exemplifies a screenshot of an embodiment of a cardiac evaluation system display showing an embodiment of a dynamic current density of an individual in atrial fibrillation 10000. Analysis and recognition of abnormal current density maps such as the one shown are achieved, for example, by comparison to normal current density maps and other abnormal current density maps with known pathology. Analysis and recognition of abnormal current density is further aided, for example, by incorporating patient biometric data such as for example heart rate, blood pressure, temperature, activity level, and heart rate variability. For example, elevated heart rate and increased heart rate variability in a patient with an abnormal current density map supports a diagnosis of arrhythmia in said patient. The devices, systems, media, and methods described herein are configured to not only identify the presence of an abnormal rhythm, but are also configured to localize the abnormality to a specific area of the cardiac anatomy. For example, area 10002 of the shown current density map is an area of abnormal current density indicating abnormal current conduction in this area of the myocardium of the atria, which is a finding consistent with atrial fibrillation. The devices, systems, media, and methods described herein are similarly configured to identify and localize abnormal areas of myocardium in other arrhythmia types such that accurate diagnosis occurs, and if ablation is indicated, accurate ablation is facilitated by the localization of the abnormality to a specific area or areas of abnormal myocardium.

VI. Computing Systems

Figure 11:
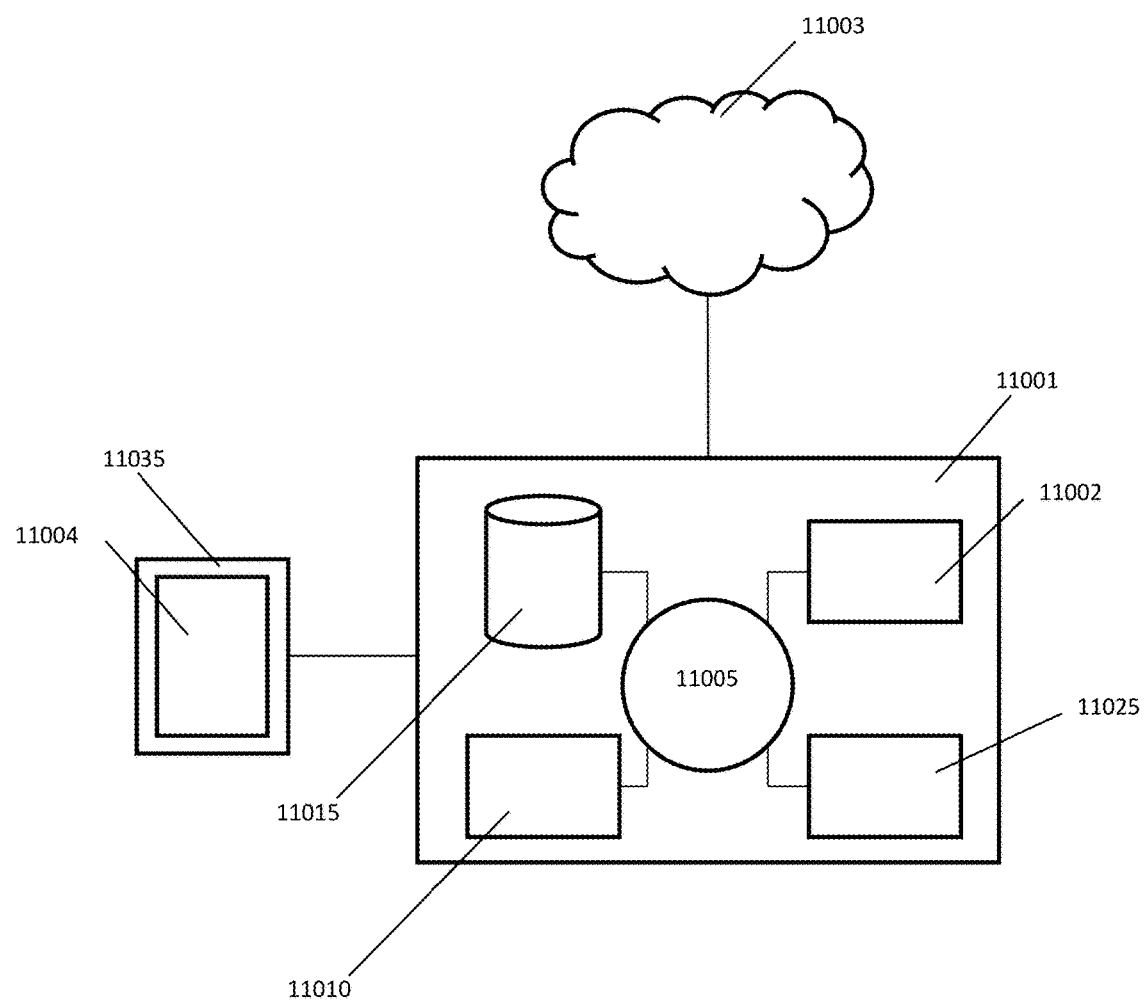
FIG. 11 exemplifies a computer system that is programmed or otherwise configured to noninvasively evaluate an organ.

FIG. 11 exemplifies a computer system 11001 that is programmed or otherwise configured to noninvasively evaluate an organ. The computer system 11001 can regulate various aspects of the evaluation device, system, media, or method of the present disclosure, such as, for example, controlling magnetic field emission, acquiring sensed data associated with an organ, analyzing the electrical current, mapping the cardiac activities on the myocardium, and etc. The computer system 11001 can be an electronic device of a user, or a computer system that is remotely located with respect to the electronic device. The electronic device can be a mobile electronic device.

The computer system 11001 includes a central processing unit (CPU, also "processor" and "computer processor" herein) 11005, which can be a single core or multi core processor, or a plurality of processors for parallel processing. The computer system 11001 also includes memory or memory location 11010 (e.g., random-access memory, read-only memory, flash memory), electronic storage unit 11015 (e.g., hard disk), communication interface 11002 (e.g., network adapter) for communicating with one or more other systems, and peripheral devices 11025, such as cache, other memory, data storage and/or electronic display adapters. The memory 11010, storage unit 11015, interface 11002 and peripheral devices 11025 are in communication with the CPU 11005 through a communication bus (solid lines), such as a motherboard. The storage unit 11015 can be a data storage unit (or data repository) for storing data. The computer system 11001 can be operatively coupled to a computer network ("network") 11003 with the aid of the communication interface 11002. The network 11003 can be the Internet, an internet and/or extranet, or an intranet and/or extranet that is in communication with the Internet. The network 11003 in some cases is a telecommunication and/or data network. The network 11003 can include one or more computer servers, which can enable distributed computing, such as cloud computing. The network 11003, in some cases with the aid of the computer system 11001, can implement a peer-to-peer network, which may enable devices coupled to the computer system 11001 to behave as a client or a server.

The CPU 11005 can execute a sequence of machine-readable instructions, which can be embodied in a program or software. The instructions may be stored in a memory location, such as the memory 11010. The instructions can be directed to the CPU 11005, which can subsequently program or otherwise configure the CPU 11005 to implement methods of the present disclosure. Examples of operations performed by the CPU 11005 can include fetch, decode, execute, and writeback.

The CPU 11005 can be part of a circuit, such as an integrated circuit. One or more other components of the system 11001 can be included in the circuit. In some cases, the circuit is an application specific integrated circuit (ASIC).

The storage unit 11015 can store files, such as drivers, libraries and saved programs. The storage unit 11015 can store user data, e.g., user preferences and user programs. The computer system 11001 in some cases can include one or more additional data storage units that are external to the computer system 11001, such as located on a remote server that is in communication with the computer system 11001 through an intranet or the Internet.

The computer system 11001 can communicate with one or more remote computer systems through the network 11003. For instance, the computer system 11001 can communicate with a remote computer system of a user (e.g., mobile device, server, etc.). Examples of remote computer systems include personal computers (e.g., portable PC), slate or tablet PC's (e.g., APPLE® iPad, SAMSUNG® Galaxy Tab), telephones, Smart phones (e.g., APPLE® iPhone, Android-enabled device, BLACKBERRY®), or personal digital assistants. The user can access the computer system 11001 via the network 11003.

Methods as described herein can be implemented by way of machine (e.g., computer processor) executable code stored on an electronic storage location of the computer system 11001, such as, for example, on the memory 11010 or electronic storage unit 11015. The machine executable or machine readable code can be provided in the form of software. During use, the code can be executed by the processor 11005. In some cases, the code can be retrieved from the storage unit 11015 and stored on the memory 11010 for ready access by the processor 11005. In some situations, the electronic storage unit 11015 can be precluded, and machine-executable instructions are stored on memory 11010.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 11001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution The computer system 11001 can include or be in communication with an electronic display 11035 that comprises a user interface (UI) 11004 for providing, for example, distributions of magnetic fields, distributions of electrical currents, distributions of local myocardial activities, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 11005. The algorithm can, for example, image acquisition, image mapping, image registration, three dimensional organ reconstruction.

While preferred embodiments of the present subject matter have been shown and described herein, it will be obvious to those skilled in the art that such embodiments are provided by way of example only. Numerous variations, changes, and substitutions will now occur to those skilled in the art without departing from the present subject matter. It should be understood that various alternatives to the embodiments of the subject matter described herein may be employed in practicing the subject matter described herein. It is intended that the following claims define the scope of the invention and that methods and structures within the scope of these claims and their equivalents be covered thereby.

What is claimed is:

1. A method for evaluating an organ in an individual in need thereof, comprising:
   a) receiving magnetic field data associated with said organ from an organ electromagnetic sensor;
   b) determining an electrical current value associated with said organ from said magnetic field data, wherein said electrical current value is determined in Ampere units or equivalent units of current measurement;
   c) determining a vector representing said electrical current value, wherein a magnitude of said vector comprises said electrical current value;
   d) identifying a position of said vector in reference to said organ; and
   e) overlaying said vector onto an image of said organ to generate an electrical current density map of said organ for use in evaluating said organ.

2. The method of claim 1, wherein evaluating said organ is non-invasive.

3. The method of claim 1, wherein said organ is a heart or a brain.

4. The method of claim 3, further comprising identifying and defining an arrhythmia in said heart.

5. The method of claim 4, further comprising identifying an arrhythmogenic focus in said heart.

6. The method of claim 3, further comprising identifying an ischemic focus in said brain.

7. The method of claim 1, further comprising calculating a plurality of distributed, spatially accurate electrical current values having dynamic, real time parameters.

8. The method of claim 1, wherein the plurality of electrical current values are in units of amperes or equivalent units of current measurement.

9. The method of claim 1, further comprising receiving said image of said organ from an imaging system.

10. The method of claim 9, wherein said imaging system comprises an ultrasound system or a fluoroscope.

11. The method of claim 9, wherein said imaging system comprises a computer tomography system or magnetic resonance system.

12. The method of claim 1, wherein said image is a three dimensional image.

13. The method of claim 12, wherein said three dimensional image is generated from two or more two dimensional images.

14. The method of claim 1, further comprising receiving demographic data associated with said individual.

15. The method of claim 14, wherein said demographic data comprises one or more of age, race, gender, and medical history of said individual.

16. The method of claim 15, wherein said received demographic data associated with said individual is used to identify a three dimensional image of an organ of a different individual, wherein the demographic data associated with said individual and demographic data associated with said different individual are essentially identical in one or more of said age, said race, said gender, and said medical history.

17. The method of claim 15, wherein said image comprises said image of said organ of said different individual.

18. The method of claim 1, further comprising receiving biometric data associated with said individual.

19. The method of claim 18, wherein said biometric data comprises one or more of heart rate, blood pressure, and temperature of said individual.

20. The method of claim 19, further comprising generating an evaluation of said organ comprising said electrical current density map and said biometric data.

\* \* \* \* \*